US 6,556,864 B1

(12) United States Patent
Picardo et al.

(10) Patent No.: US 6,556,864 B1
(45) Date of Patent: Apr. 29, 2003

(54) OBJECT ACTIVATED DEFIBRILLATOR

(75) Inventors: Anthony G. Picardo, Tacoma, WA (US); Thomas Allen Solosko, Issaquah, WA (US); Kim J. Hansen, Renton, WA (US); Christine Janae, Seattle, WA (US); Paul I. Szabo, Seattle, WA (US); John A. Moren, Edmonds, WA (US); Daniel J Powers, Issaquah, WA (US); Joseph R. Diederichs, Seattle, WA (US); Ian G. MacDuff, Bothell, WA (US); Steven Ranta, Seattle, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/712,001

(22) Filed: Nov. 13, 2000

(51) Int. Cl.⁷ .................................................. A61N 1/39
(52) U.S. Cl. ............................................. 607/5; 607/63
(58) Field of Search ........................... 607/5, 9, 63, 28, 607/27, 37

(56) References Cited

U.S. PATENT DOCUMENTS

| 5,607,454 A | 3/1997 | Cameron et al. |
| 5,735,879 A | 4/1998 | Gliner et al. |
| 5,800,460 A | 9/1998 | Powers et al. |
| 5,836,993 A | 11/1998 | Cole |
| 5,868,792 A | 2/1999 | Ochs et al. |
| 5,879,374 A | 3/1999 | Powers et al. |
| 5,899,926 A | 5/1999 | Ochs et al. |
| 5,951,598 A | 9/1999 | Bishay et al. |
| 6,048,218 A | 4/2000 | Greenstein |
| 6,304,783 B1 | * 10/2001 | Lyster et al. |

OTHER PUBLICATIONS

Doherty, Alidene, et al., Supplement to Circulation, vol. 96, No. 8, Oct. 21, 1997, Abstracts From the 70th Scientific Sessions, Study Presented at the AHA Annual Scientific Session in Orlando, Florida Abstract No. 2041 (Nov. 1977).

* cited by examiner

Primary Examiner—Scott M. Getzow

(57) ABSTRACT

An apparatus for delivering defibrillation therapy to a patient. Specifically, an external defibrillators or automatic or semi-automatic external defibrillator (AEDs) is described. The defibrillator is automatically activated or inactivated by, for example, inserting or removing an object, such as a plug or a pin, into a receptacle within the defibrillator housing.

20 Claims, 4 Drawing Sheets

OBJECT ACTIVATED DEFIBRILLATOR

FIELD OF THE INVENTION

This invention relates generally to an apparatus for delivering defibrillation therapy to a patient. Specifically, this invention relates to external defibrillators, more specifically this invention relates to automatic or semi-automatic external defibrillators (AEDs). Further this invention relates to a defibrillator that is automatically activated or inactivated by, for example, inserting or removing an object, such as a plug or a pin, from a receptacle.

BACKGROUND OF THE INVENTION

Sudden cardiac death (SCD) is the leading cause of death in the United States. On average, 1000 people per day die; this translates into one death every two minutes. Most SCD is caused by ventricular fibrillation ("VF"), in which the heart's muscle fibers contract without coordination, thereby interrupting normal blood flow to the body. The only effective treatment for VF is electrical defibrillation, which applies an electrical shock to the patient's heart. The electrical shock clears the heart of the abnormal electrical activity (in a process called "defibrillation") by depolarizing a critical mass of myocardial cells to allow spontaneous organized myocardial depolarization to resume.

To be effective, the defibrillation shock must be delivered to the patient within minutes of the onset of VF. Studies have shown that defibrillation shocks delivered within one minute after the onset of VF achieves up to a 100% survival rate. However, the survival rate falls to approximately 30% after only 6 minutes. Beyond 12 minutes, the survival rate approaches zero. Importantly, the more time that passes, the longer the brain is deprived of oxygen and the more likely that brain damage will result.

Historically, the size and weight of external defibrillators has limited its utility for rapid response by emergency medical response teams. Traditional manually operated monophasic defibrillators require a high degree of skill to operate and thus are typically reserved to the hospital environment. Automatic and semi-automatic external defibrillators (AEDs) provide on-board algorithms to evaluate the cardiac rhythm; these algorithms enable the device to evaluate the appropriateness of administering defibrillation therapy to a patient. An additional factor that has helped to increase the availability of defibrillators in the field is the use of lower energy therapeutic energy pulses. For example, Gliner et al., U.S. Pat. No. 5,607,454 entitled "Electrotherapy Method and Apparatus" and incorporated herein, describes an external defibrillator capable of delivering an impedance compensated biphasic waveform. The use of a biphasic waveform considerably lowers the energy required to defibrillate a patient from the standard 200-300-360J used in monophasic external defibrillators to 150J. This enables the device to achieve a lower weight (4 lbs.) than possible for traditional monophasic devices, which typically weigh in excess of 8 lbs. The advancements taught by Gliner et al. are embodied, for example, in the ForeRunner® AED and the FR2 AED by Agilent Technologies, Palo Alto, Calif.

Although currently available AEDs are considered to be extremely safe to use and deploy, changes to the human factor designs may further ensure correct usage by a minimally trained, infrequent user particularly when such users are under highly stressed conditions. For example, a serious concern existed over whether minimally trained, infrequent users would be able to correctly apply electrode pads following training. In a study performed by Alidene Doherty and presented at the AHA Annual Scientific Session in Orlando, Fla. (November 1997), Abstract No. 2041, it was noted that six months after training first responders had a 67–90% accuracy rate in placing traditional disposable electrode pads on a patient. However, the study also demonstrated that there was a 100% retention of correct pad placement for the electrode pads taught by U.S. Pat. No. 5,951,598 to Bishay et al. entitled "Electrode System," the specification of which is incorporated herein.

There are remaining issues concerning deployment of defibrillators by first responders. For example, will the first responders recall the correct deployment sequence? The step of calling for emergency services, or "911," is an important step that may be inadvertently skipped when an inexperienced lay responder is responding to an emergency. Another concern relates to the possibility that a lay responder could inadvertently turn off the AED at an inappropriate time during the rescue. As defibrillators, particularly AEDs, become increasingly available, it becomes increasingly important to focus design considerations on the human factors that may lead to errors during actual use.

Thus, what is needed, is a method and apparatus for delivering therapy to a patient that addresses the possibility of human error when the device is deployed by a minimally trained, infrequent user.

SUMMARY OF THE INVENTION

A defibrillator is provided that has a housing; a high voltage delivery system comprising an energy source and a switch connecting the energy source to an exterior of the housing of the defibrillator; a controller operably connected to the high voltage delivery system; a receptacle within the housing, accessible from the exterior of the housing; and a removable object within the receptacle which changes the operation mode of the defibrillator upon removal. The receptacle may be an electrode receptacle, or other suitable receptacle. The object may be a pin, plug, electrode connector, or other suitable object. The object may also be connected to the defibrillator by a tether. Removal of the object into the receptacle changes the operation of the defibrillator. For example, the operation mode may change from a sleep mode to an on mode, or an off mode to an on mode. Additionally, the defibrillator may be set-up to begin delivering user instructions when the operation mode is changed to the on mode.

Another defibrillator is provided that has a housing; a high voltage delivery system comprising an energy source and a switch connecting the energy source to an exterior of the housing of the defibrillator; a controller operably connected to the high voltage delivery system; a receptacle within the housing, accessible from the exterior of the housing; and an insertable object that changes the operation mode of the defibrillator upon insertion. The receptacle may be an electrode receptacle, or any other suitable receptacle. The object may be a pin, plug, electrode connector, or any other suitable object. The object may also be connected to the defibrillator by a tether. When the object is inserted, the operation of the defibrillator changes. For example, the operation mode may change from a sleep mode to an on mode, or may change from an off mode to an on mode. When the operation mode is changed, the defibrillator may begin delivering user instructions.

A method of operating a defibrillator is also provided. This method includes removing a removable object from a receptacle in the defibrillator housing; automatically changing the operation mode of the defibrillator in response to the removal of the removable object; and delivering instructions to a user. The method may also include changing the operation mode of the defibrillator from a sleep mode to an on mode, or from an off mode to an on mode.

Another method includes: inserting an insertable object into a receptacle in the defibrillator housing; automatically changing the operation mode of the defibrillator in response to the insertion of the removable object; and delivering instructions to a user. The method may also include changing the operation mode of the defibrillator from a sleep mode to an on mode, or from an off mode to an on mode.

BRIEF DESCRIPTION OF THE DRAWINGS

In FIG. 1A, a removable object is shown inserted into a receptacle in the defibrillator housing. In FIG. 1B, the object is shown removed from the receptacle. In FIG. 1C the electrodes are illustrated in a pre-connected arrangement and a removable object is shown inserted into an auxiliary socket.

DETAILED DESCRIPTION OF THE PREFERRED EMBODIMENT

The following discussion is presented to enable a person skilled in the art to make and use the invention. Various modifications to the preferred embodiment will be readily apparent to those skilled in the art, and the generic principles herein may be applied to other embodiments and applications without departing from the spirit and scope of the present invention as defined by the appended claims. Thus, the present invention is not intended to be limited to the embodiment show, but is to be accorded the widest scope consistent with the principles and features disclosed herein.

Figure 1A:
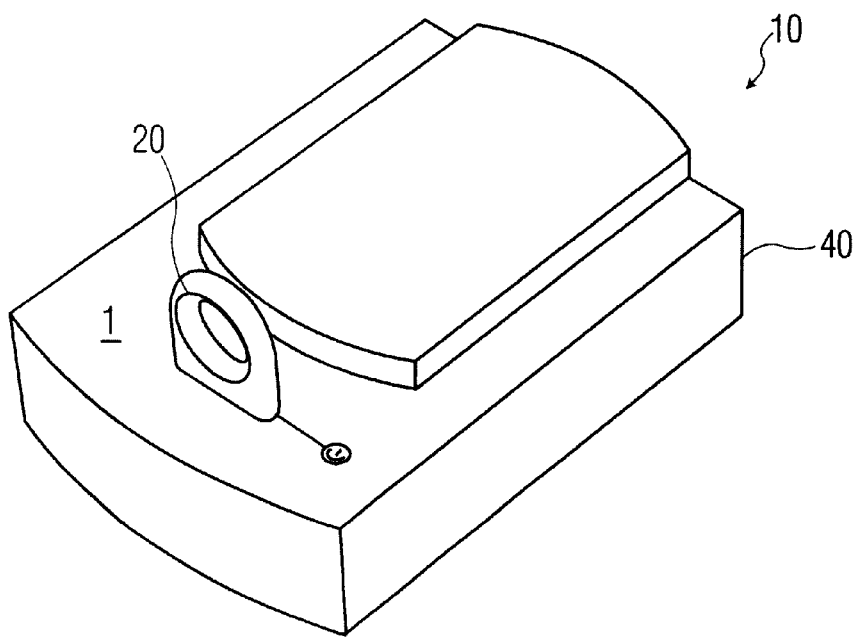
FIGS. 1A through 1C are top perspective views of a defibrillator according to one embodiment of this invention.

FIG. 1A is a perspective top view of a defibrillator 10. The defibrillator 10 has a removable object 20 inserted into a receptacle 30 within the defibrillator housing 40. In one embodiment, removing the object 20 from the receptacle activates the "on" sequence of the defibrillator 10. In yet another embodiment, inserting the object 20 into the receptacle could inactivate the defibrillator. In another embodiment, inserting the object 20 into the receptacle 30 could activate the "on" sequence for the defibrillator 10. Alternatively, removing the object 20 could inactivate the defibrillator. As will be appreciated by those of skill in the art, these embodiments can be combined. For example, inserting the object for activation could be combined with removing the object for inactivation.

A suitable object 20 could take a variety of forms and shapes. For example, a pin or a plug might be appropriate. Further it may be appropriate to have the object attached to the device, such as by a tether, or other suitable mechanism (not shown), so that when the object 20 is removed, the object 20 will not inadvertently be lost.

Once the "on" sequence of the defibrillator 10 has been activated (by either inserting or removing the object 20), the defibrillator 10 changes state. In one embodiment, for example, the defibrillator 10 could change from a self-monitoring mode to an ON mode. In that scenario, when the defibrillator 10 is in the self-monitoring mode, the defibrillator 10 performs tests on its systems, such as those tests described in U.S. Pat. No. 5,800,460 to Powers et al. for "Method for Performing Self Test in a Defibrillator," U.S. Pat. No. 5,868,792 to Ochs et al. for "Environment-Response Method for Maintaining Electronic Device Such as an External Defibrillator," and U.S. Pat. No. 5,899,926 by Ochs et al for "Method and Apparatus for Aperiodic Self-Testing of a Defibrillator," the specifications of which are incorporated herein, to ensure its readiness for deployment.

In another embodiment, the defibrillator 10 could change from a sleep mode to an ON mode, or could change from a OFF mode (i.e., power off) to an ON mode. Once the defibrillator mode has changed, the defibrillator 10 then begins its operation. The defibrillator 10 could first run a power-on test to ensure device availability prior to beginning to deliver user instructions, or could begin delivery of user instructions immediately.

As will be appreciated by those of skill in the art, the step of removing the 10 object 20 from the receptacle 30 may replace the step of powering on the defibrillator 10. Alternatively, the step of removing the object may act as a pre-initiation step in which the defibrillator 10 then instructs the user to activate the defibrillator (i.e., press the on button). In the preferred embodiment, however, it will be appreciated that the step of removing the object 20 from the receptacle will eliminate the need for separately turning-on the defibrillator.

Where the reverse operation is performed, i.e., insertion of the object 20 into the receptacle 30 is the step that activates the defibrillator 10, inserting the object 20 could act as an initiation step, or pre-initiation step, as described above.

Figure 1B:
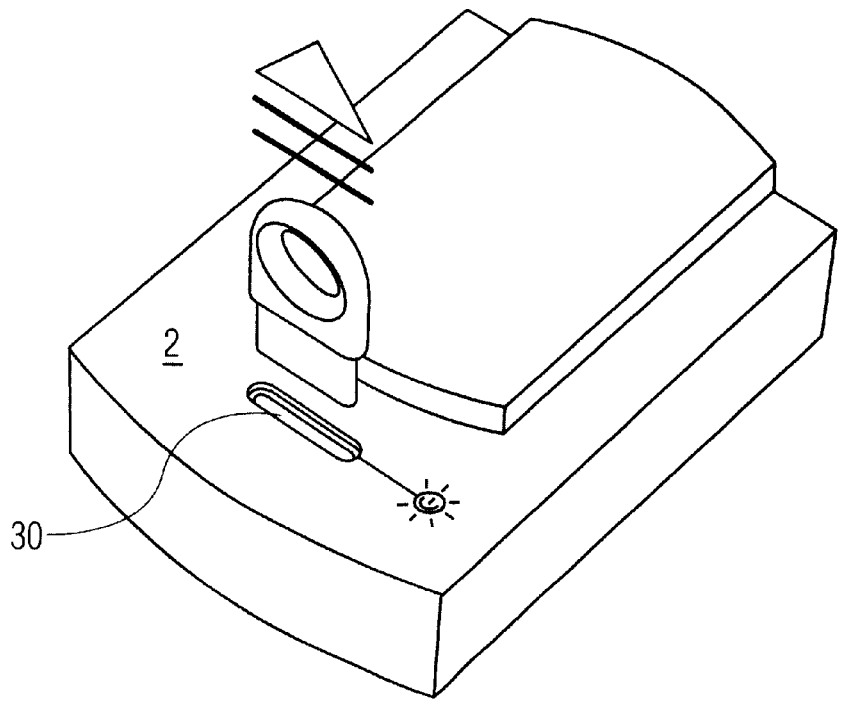

FIG. 1B illustrates the defibrillator 10 with the object 20 removed from the receptacle. As will be appreciated by those of skill in the art, the receptacle could be designed solely to receive the object 20, or it could be the female electrode connector receiving housing into which the defibrillation electrodes would then be plugged.

Figure 2:
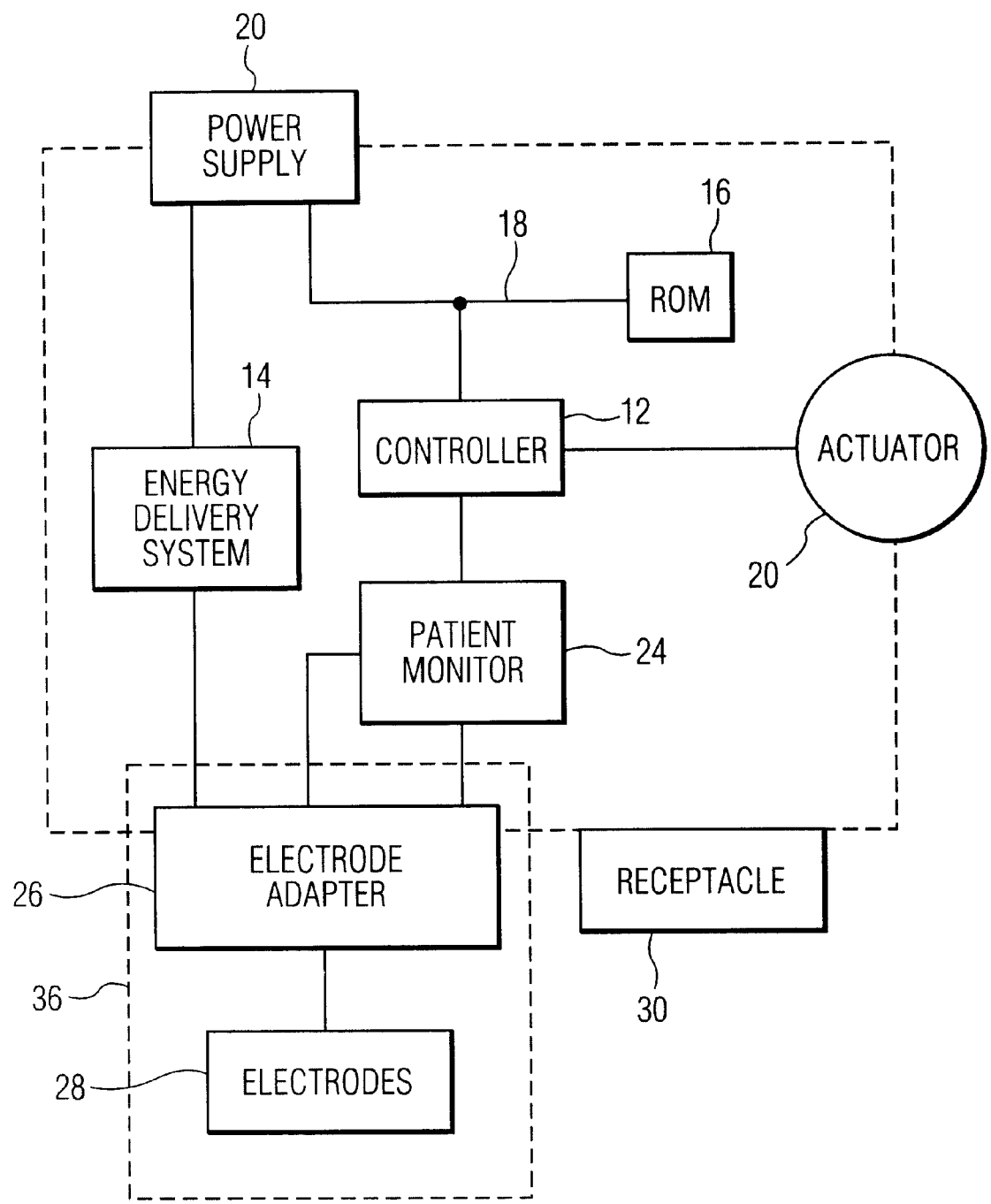
FIG. 2 is a high-level, functional block diagram of a defibrillator.

FIG. 2 is a block diagram showing a device 10. Device 10 is an electrotherapy device. The device 10 may be include the ability to defibrillate, cardiovert, or pace a patient, or a combination of these features. Device 10 has a controller 12 that operates an energy delivery system 14 and performs other aspects of the operation of the device. Software instructions for the operation of the device are accessible from read only memory (ROM), such as incorporated ROM 16. The controller accesses instructions for operation from ROM 16. It should be understood that, in this and other embodiments described below, "controller" means a microprocessor, controller, gate array, other control logic, or any combination of these elements.

Controller 12 communicates with ROM 16 via a memory bus 18. Electrode system 36 includes electrodes 28 and an electrode adapter 26.

Figure 3:
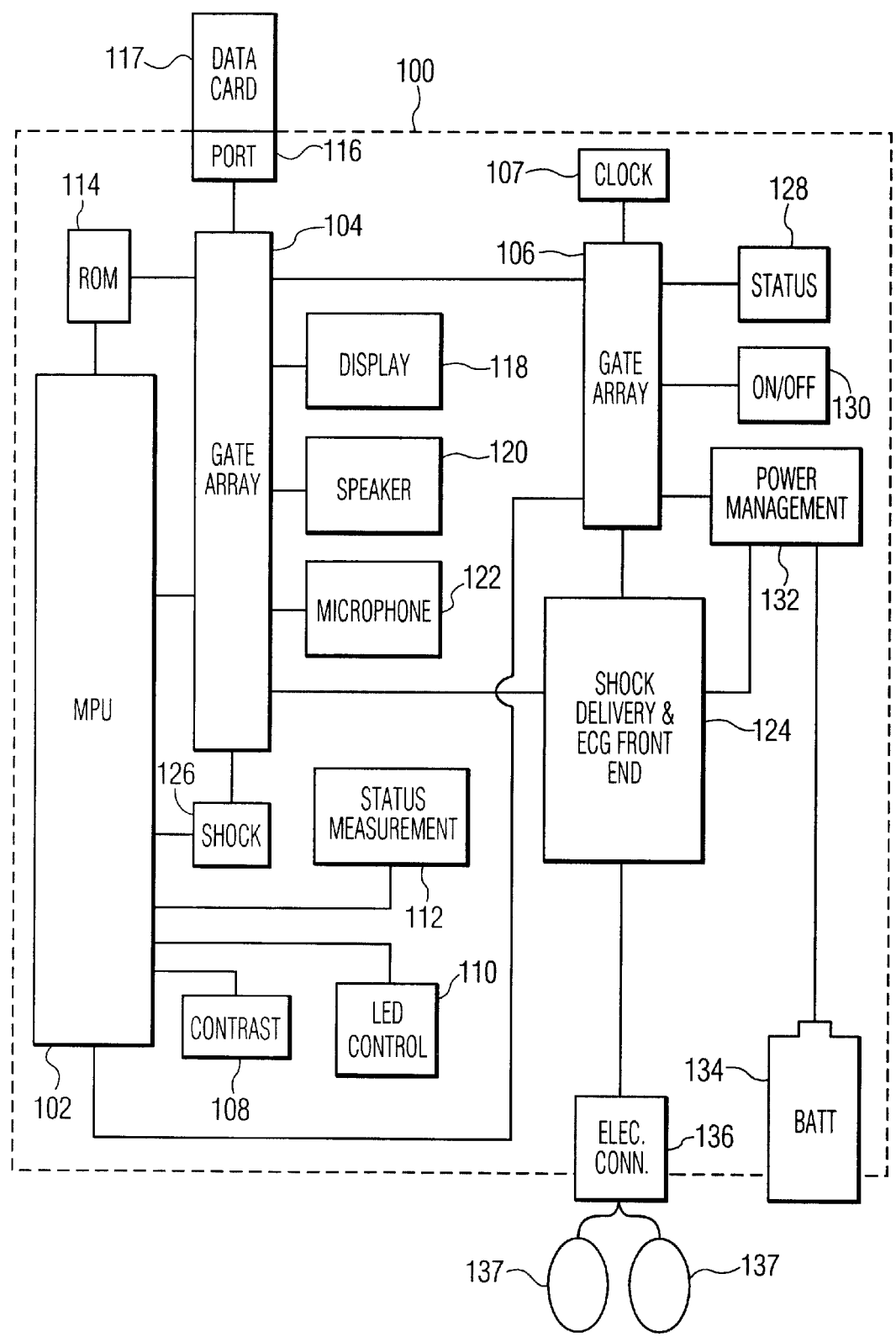
FIG. 3 is a schematic diagram showing a circuit capable of delivering a biphasic waveform of the invention.

The major components of an AED are shown in FIG. 3 in block diagram form. Further detailed information about the operation of an AED can be obtained in U.S. Pat. No. 5,836,993, to Cole for "Electrotherapy Device Control System and Method," the specification of which is incorporated herein. As will be appreciated by those of skill in the art, the invention can be used in a variety of AEDs and is not limited to this configuration, which is used for illustration purposes only.

In this illustration, defibrillator control functions are divided among a microprocessor unit (MPU) 102 and two custom gate arrays 104 and 106.

MPU 102 performs program steps according to software instructions provided to it from ROM 114. MPU 102 controls the operation of certain buttons (such as display contrast buttons 108) and certain system LED's 110 (such as LED's associated with the shock button and the electrode connector). MPU 102 also receives system status information as shown by block 112.

Gate array 104 implements the memory map to system ROM 114. System ROM 114 is preferably flash ROM, although EPROM or any other electrically erasable and programmable nonvolatile memory could be used. Gate array 104 also controls a display 118, a speaker 120, and a microphone 122. Gate array 104 can actuate a relay within the shock delivery and ECG front-end system 124 in response to actuation of a shock button 126 by a user during treatment mode.

Gate array 106 provides a system monitor function by performing automatic self-tests of the defibrillator and its components. The gate array 106 displays the operational status of the defibrillator on a status display 128. Details of suitable self-tests may be found in U.S. Pat. No. 5,879,374, to Powers, et al. for "External Defibrillator with Automated Self-Testing Prior to Use," the specification of which is incorporated herein by reference. Gate array 106 is also the defibrillator's interface with a user-activated on/off switch 130. Gate array 106 controls the power management subsystem 132 to provide power to operate system components from power supply 134 and to provide energy to the shock delivery system's capacitor(s) for a therapeutic shock during treatment mode. Gate array 106 also interfaces with the defibrillator's ECG front end, enables the shock delivery system to deliver a shock in response to detection of a patient ECG pattern requiring treatment (and actuation of the shock button), and controls delivery of the shock to electrode connector 136 in response to shock delivery status information obtained during delivery of the shock. Further information regarding this last function may be found in U.S. Pat. No. 5,735,879 to Gliner et al. for "Electrotherapy Method for External Defibrillators," and U.S. Pat. No. 5,607,454, to Cameron et al. for "Electrotherapy Method and Apparatus," the specifications of which are incorporated herein.

As described previously, electrical connector 136 may communicate directly with MPU 102 to identify the electrode type, or electrical connector 136 may communicate with MPU 102 via an identifier receiver that interfaces between the MPU 102 and the identifier of the electrical connector 136. For example, in the optical encoding solution, the photodetectors could act as an identifier receiver in communication between the MPU 102 and the electrical connector 136.

These defibrillator components communicate with each other over suitable communication buses, as shown.

In one embodiment, the object 20 is a plug and the plug is inserted into the female opening designed to engage the electrode cable connector. [See, U.S. Pat. No. 6,048,218 to Greenstein for "Medical Electrode System," the specification of which is incorporated herein for further information pertaining to construction of a suitable cable connector system.]

The advantage of this embodiment, is that the patient connector socket is protected when the defibrillator is not in use. This can be particularly important where the connector system is not designed to remove debris (as provided for in Greenstein). Another advantage is that the plug provides a physical barrier; preventing the user from touching the pins within the patient connector socket. This, in turn, enables the AED to test the electrode pins during a high voltage self-test without risk of causing injury. See, e.g., Powers and Ochs, infra, for more information on self-tests.

Turning now to possible operations of the devices employing the use of a removable object that is REMOVED to activate the ON sequence, in a first operation, removal of the object turns on the defibrillator. It is expected that automatic turning on of the defibrillator in response to removal of the plug would improve the user interface by providing an intuitive method of actuating the defibrillator. In this embodiment, the step of removing the object also replaces the step of pressing a button to activate the AED with a more intuitive step. Another advantage is that the use of an object, such as a plug, enables the defibrillator to be safely transported without risk of accidentally activating the defibrillator.

In another operation, removal of the object activates a pre-initiation sequence wherein the defibrillator instructs the user to "press the ON button." The use of a removable object for initiation of a pre-initiation sequence would likely have the same effect on the intuitiveness of the device. However, as will be appreciated by those of skill in the art, in this embodiment, if a user pressed the ON button without first removing the plug, the device may be configured to instruct the user to remove the object. This would particularly be true in the situation where the object receptacle was also the electrode receptacle or where insertion of the object inactivates the defibrillator.

In another operation, which could be used with any of the previous operations, replacement of the object within the patient connector could function to turn the device off, thus replacing the OFF button. The advantage to this design is that it eliminates the possibility of inadvertently turning the device OFF during an emergency; for example if a user were to press the OFF button instead of the SHOCK button.

Figure 1C:
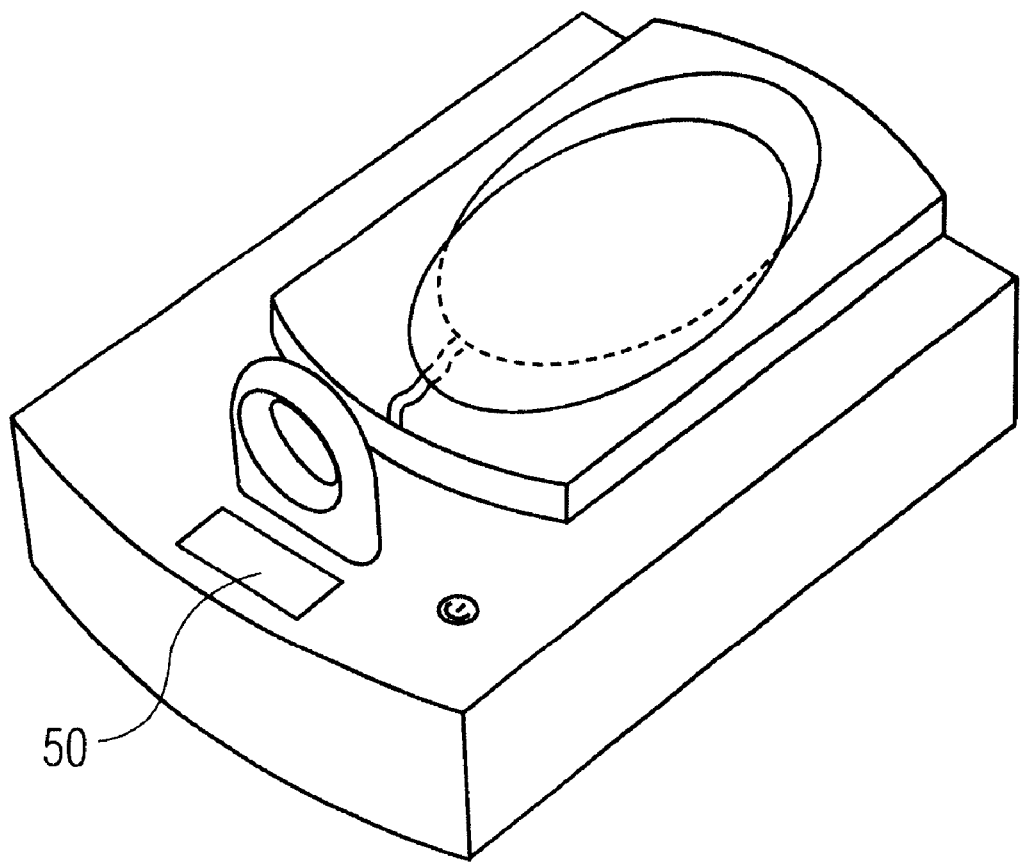

In another embodiment, the plug would be inserted and removed from an auxiliary socket 50. A defibrillator having an auxiliary socket is depicted in FIG. 1C. An auxiliary plug may be used where, for example, the electrodes are pre-connected to the defibrillator (as shown in FIG. 1C). However, as will be appreciated by those of skill in the art, an auxiliary plug may be employed even where the electrodes are not pre-connected.

Turning now to possible operations of the devices employing the use of a removable object that is INSERTED to activate the ON sequence, in a first operation, insertion of the object turns on the defibrillator. It is expected that automatic turning on of the defibrillator in response to insertion of the plug may improve the user interface by providing an intuitive method of actuating the defibrillator. In this embodiment, the step of inserting the object also replaces the step of pressing a button to activate the AED.

In another operation, insertion of the object activates a pre-initiation sequence wherein the defibrillator instructs the user to "press the ON button." The use of an insertable object for initiation of a pre-initiation sequence would likely have the same effect on the intuitiveness of the device. However, as will be appreciated by those of skill in the art, in this embodiment, if a user pressed the ON button without first inserting the plug, the device may be configured to first instruct the user to insert the object.

In another operation, which could be used with any of the previous operations, removal of the object within the patient connector could function to turn the device off, thus replacing the OFF button. The advantage to this design is that it eliminates the possibility of inadvertently turning the device OFF during an emergency; for example if a user were to press the OFF button instead of the SHOCK button.

What is claimed is:

1. A defibrillator comprising:
    a housing;
    a high voltage delivery system comprising an energy source and a switch connecting the energy source to an exterior of the housing of the defibrillator;
    a controller operably connected to the high voltage delivery system;
    a receptacle within the housing, accessible from the exterior of the housing; and
    a removable object within the receptacle which changes the operation mode of the defibrillator upon removal.
2. The defibrillator of claim 1 wherein the receptacle is an electrode receptacle.
3. The defibrillator of claim 1 wherein the object is selected from the group consisting of pin, plug, and electrode connector.
4. The defibrillator of claim 1 wherein the object is connected to the defibrillator by a tether.
5. The defibrillator of claim 1 wherein the operation mode of the defibrillator changes from a sleep mode to an on mode.
6. The defibrillator of claim 1 wherein the operation mode of the defibrillator changes from an off mode to an on mode.
7. The defibrillator of claims 5 or 6 wherein the defibrillator begins to deliver user instructions when the operation mode is changed to the on mode.
8. A defibrillator comprising:
    a housing;
    a high voltage delivery system comprising an energy source and a switch connecting the energy source to an exterior of the housing of the defibrillator;
    a controller operably connected to the high voltage delivery system;
    a receptacle within the housing, accessible from the exterior of the housing; and
    an insertable object that changes the operation mode of the defibrillator upon insertion.
9. The defibrillator of claim 8 wherein the receptacle is an electrode receptacle.
10. The defibrillator of claim 8 wherein the object is selected from the group consisting of pin, plug, and electrode connector.
11. The defibrillator of claim 8 wherein the object is connected to the defibrillator by a tether.
12. The defibrillator of claim 8 wherein the operation mode of the defibrillator changes from a sleep mode to an on mode.
13. The defibrillator of claim 8 wherein the operation mode of the defibrillator changes from an off mode to an on mode.
14. The defibrillator of claims 12 or 13 wherein the defibrillator begins to deliver user instructions when the operation mode is changed to the on mode.
15. A method of operating a defibrillator comprising:
    removing a removable object from a receptacle in the defibrillator housing;
    automatically changing the operation mode of the defibrillator in response to the removal of the removable object; and
    delivering instructions to a user.
16. The method of claim 15 further comprising the step of changing the operation mode of the defibrillator from a sleep mode to an on mode.
17. The method of claim 15 further comprising the step of changing the operation mode of the defibrillator from an off mode to an on mode.
18. A method of operating a defibrillator comprising:
    inserting an insertable object into a receptacle in the defibrillator housing;
    automatically changing the operation mode of the defibrillator in response to the insertion of the removable object; and
    delivering instructions to a user.
19. The method of claim 18 further comprising the step of changing the operation mode of the defibrillator from a sleep mode to an on mode.
20. The method of claim 18 further comprising the step of changing the operation mode of the defibrillator from an off mode to an on mode.

* * * * *